United States Patent [19]

Dartnell et al.

[11] Patent Number: 5,252,555

[45] Date of Patent: Oct. 12, 1993

[54] MICROEMULSION CONTAINING A PERFUMING CONCENTRATE AND CORRESPONDING PRODUCT

[75] Inventors: Nathalie Dartnell, Paris; Bernard Breda, Bougival, both of France

[73] Assignee: Yves Saint Laurent Parfumes, Neuilly sur Seine, France

[21] Appl. No.: 889,277

[22] Filed: May 28, 1992

[30] Foreign Application Priority Data

May 31, 1991 [FR] France ................................ 91 06592

[51] Int. Cl.$^5$ .............................................. A61K 7/46
[52] U.S. Cl. .......................................... 512/4; 512/2
[58] Field of Search ......................................... 512/4, 2

[56] References Cited

FOREIGN PATENT DOCUMENTS

| | | | |
|---|---|---|---|
| 278660 | 8/1988 | European Pat. Off. | 252/312 |
| 334777 | 9/1989 | European Pat. Off. | 252/312 |
| 368146 | 5/1990 | European Pat. Off. | 512/1 |
| 2190681 | 11/1987 | United Kingdom | 512/3 |

OTHER PUBLICATIONS

Schick, et al., *Surfactant Sciences Series*, vol. 6, *Emulsions & Emulsion Technology*, Pt. II, Dekker Inc., New York, Chapter 13, "Cosmetic Emulsions," p. 917.

*Primary Examiner*—James H. Reamer
*Attorney, Agent, or Firm*—Pollock, VandeSande & Priddy

[57] ABSTRACT

The invention relates to a non-alcoholic perfuming product comprising a lipophilic phase based on a concentrate of odoriferous substance or perfume and a water-soluble phase, the said phases being combined in a microemulsion and the content of concentrate of odoriferous substances being between approximately 5 and 50% by weight of the product, a surfactant based on polyethylene glycol, a first cosurfactant based on polyglycerol and a second cosurfactant based on ether phosphate also being combined in the microemulsion.

Application to the production of cosmetic products.

12 Claims, No Drawings

MICROEMULSION CONTAINING A PERFUMING CONCENTRATE AND CORRESPONDING PRODUCT

The invention relates, generally speaking, to a perfuming compound for cosmetic use (including pharmaceutical use) which can have a relatively high concentration of perfume concentrate, with a transparent appearance resembling that of conventional perfuming products of an alcoholic nature.

As is known, "cosmetic" perfumes are nowadays products sold under the name "perfume" or "extract", and contain a relatively high concentration, usually of the order of 15 to 30%, of a mixture of natural or synthetic odoriferous products, dissolved in an alcohol such as ethyl alcohol, and sometimes other solvents, with or without the addition of water or other adjuvants.

Other currently known perfuming products such as "toilet perfumes" or "perfume waters" and "toilet waters" possess overall, generally speaking, the same perfume composition, but contain lower concentrations of odoriferous substances, usually dissolved in a less concentrated alcohol. Generally speaking, toilet perfumes or perfume waters are considered to possess a concentration of perfume products of between approximately 8 and 15%, while toilet waters possess a concentration generally of the order of 4 to 8% (by weight of the perfuming product).

It nevertheless proves to be the case that the presence of still relatively high concentrations of alcohol in current perfuming products considerably limits their use.

In effect, alcohol is known to be a skin irritant, in the sense that it dehydrates the skin by removal of the hydrolipid film covering and protecting the skin surface. It constitutes, in addition, a primary eye irritant, and tends to promote dandruff formation in contact with the hair, dulling the hair, furthermore, and making it dry and brittle by disorganizing the cuticle and removing the protective sebaceous coating.

Nevertheless, as is known, alcohol is traditionally considered to be almost the only chemical compound permitting the solubilization of perfume concentrates of an exclusively lipophilic nature in a single homogeneous and transparent phase, these perfume concentrates (or odoriferous substances) often being obtained by solvent extraction or by distillation of substances of vegetable or animal origin, or even from synthetic products.

Now, the subject of the invention is precisely a non-alcoholic perfuming product which is advantageously transparent and stable in character, safe to use, very well tolerated by the skin, virtually non-toxic and practically void of detergent action.

In the context of the invention, the perfuming product in question will be considered to be non-alcoholic inasmuch as it contains no saturated hydrocarbon with a number of carbon atoms below 10 or above 20 and bearing a hydroxyl function replacing a hydrogen atom or function (ethanol being a typical example of such an alcohol).

Since the product in question has to be able, where appropriate, to be diffused into the hair as a perfuming product without causing irritation or degradation, it became apparent, furthermore, that it was really necessary to avoid the use of alcoholic compounds.

Thus, the invention proposes, more specifically, a non-alcoholic perfuming cosmetic product comprising a hydrophilic phase and a lipophilic phase containing a concentrate of perfume(s) or odoriferous substances, these phases being combined in a microemulsion and the content of odoriferous substances preferably being between approximately 5 and 50% by weight of the product.

It will be noted at once that a distinction should be made, in the cosmetic field, between microemulsions for use (as in the present instance) in perfuming products and the more conventional "perfumed" microemulsions in which the perfume concentrate is added only in low concentrations (for example of the order of 1 to 3% approximately) with the main object of covering the residual odor linked to the raw materials of which the microemulsion is composed.

And it is all the more necessary to make this distinction, inasmuch as it was found that an increase in the perfume concentration in a microemulsion up to doses capable of being very large leads to increased problems of solubility of the perfume concentrate in this microemulsion and of stability of the latter, as well as to oxidation problems promoted by the water-soluble phase often consisting of water, these problems naturally not being encountered in the context of alcoholic products.

In combination with the abovementioned perfuming product, the invention hence relates quite naturally to the microemulsion containing the perfuming concentrate.

In the present instance, this microemulsion is characterized in that it comprises, mixed:

an aqueous or hydrophilic phase, a fatty phase of lipophilic nature, comprising a perfuming concentrate consisting of odoriferous substances, at least one surfactant or emulsifier based on polyethylene glycol, a first cosurfactant (or co-emulsifier) based on polyglycerol, and a second cosurfactant (or co-emulsifier) based on ether phosphate.

The above microemulsion naturally consists of a homogeneous and virtually transparent micellar solution containing particles between approximately 5 and 500 angstroms ($10^{-10}$ m) in size.

It is also clear that both the surfactant and the two cosurfactants are employed here essentially as emulsifying agents, or even as emulsion stabilisers or viscosity-enhancing agents. A list of such agents is supplied in the CTFA manual of cosmetic ingredients (pages 90 to 94).

If reference is made, in particular, to European Patent Application EP-A-0, 334,777, it may be established that it was already known to use, in particular in the cosmetics industry, a microemulsion comprising, as in the present instance, a hydrophilic phase (such as water, glycols, glycerol or mixtures of these compounds), a surfactant based on polyethylene glycol and a cosurfactant based on polyglycerol.

However, it will be established that, in this document, the hydrophilic phase was necessarily combined with an oily phase of lipophilic nature, such as a mineral, vegetable, animal or synthetic oil.

Now, in the context of the invention, it was found that such a lipid portion was not essential, since it could be replaced by a fatty phase of lipophilic nature containing the selected perfume concentrate and could be non-lipid in its overall nature.

In order to avoid any misunderstanding, the definition of lipophilic will apply to a molecular group which is non-polar overall, at which attractions or affinities are exerted especially towards the molecules of an organic medium having predominant hydrophobic character, and in particular lipids, these lipids being defined as lipophilic substances which are insoluble in water and soluble in benzene and ether, and contain one or more fatty acids or fatty acid derivatives such as esters, alcohols and aldehydes.

In the publication EP-A-0,334,777, it is also stated that if the "surfactants" are chemical compounds having pronounced hydrophilic character, their use will result only in micelle formation, a surfactant employed alone in this way solely permitting a micellar solution to be formed, while the cosurfactants are more hydrophobic in character and their use will result, more especially, in causing the mutual solubilization of the phases of the microemulsion.

Still in this document, it is stated, in addition, that the combination of a surfactant based on polyethylene glycol and a cosurfactant based on polyglycerol enables a thermally and mechanically stable microemulsion to be obtained.

However, there is no indication that such stability could also be achieved in the presence of an advantageously non-lipid lipophilic phase essentially based, furthermore, on a perfuming concentrate capable of reaching approximately 50% by weight of the product or of the microemulsion.

Now, it proved to be the case that, even essentially in the absence of alcohol (see definition given previously), such a compound remained stable both thermally and mechanically.

It was also found that, in the microemulsion of the invention, the presence of a second cosurfactant based on ether phosphate further promoted the solubilisation of the compounds and the overall stability of the microemulsion.

Furthermore, a marked decrease in oxidation problems was noted, these problems being increased in the present instance on account of the hydrophilic phase, which can be very largely based on water or on aqueous compounds.

An explanation which is advanced is that this second cosurfactant (or co-emulsifier), inasmuch as it enables the stability to be enhanced, in particular in the high contents of perfuming compound, would enable the micelles of this microemulsion to "coat" the concentrate in question better and hence to protect it both against external (in particular ultraviolet) radiation and against the hydrophilic medium, especially if it is aqueous.

The microemulsion thereby obtained is hence very safe to use, very well tolerated by the skin and virtually non-toxic, and has practically no detergent action.

For the definition of all these expressions, reference may advantageously be made, if necessary, to the abovementioned publication EP-A-0,334,777.

As regards the surfactant or emulsifier used, it will also be noted that the latter is advantageously a mixed ester of glycerol and polyethylene glycol, present to the extent of at least approximately 10% by weight of the mixture, this boundary value being dictated in practice by the fact that, below this content, there is a tendency to obtain simply a traditional, that is to say opaque, emulsion instead of a microemulsion. As regards the maximum content, this will be essentially dictated by the concentration of concentrate of odoriferous substances, thus being capable of reaching 50% (or even more) by weight of the mixture. In this surfactant, the polyethylene glycol will advantageously have an average molecular weight of between 100 and 1000, and preferably of the order of 400, endowing it with a completely non-detergent character.

As regards the first emulsion cosurfactant, the choice will preferably fall on an ester of polyglycerol and liquid fatty acids, in a smaller proportion in the mixture than that of the abovementioned surfactant.

Advantageously in this first cosurfactant, the polyglycerol will have a molecular weight of between approximately 100 and 1000 and the fatty acid may, for example, consist of oleic acid or isostearic acid, alone or mixed.

Regarding content, that of the first cosurfactant will preferably be between approximately 1 and 20% by weight of the mixture.

As a second cosurfactant, the use of an alkyl ether phosphate based on polyethoxylated fatty alcohols, combined in the mixture in a proportion which is preferably smaller than that of the surfactant, was found to be advisable.

Regarding concentration, a content of the second cosurfactant of between approximately 0.5 and 15% by weight of the mixture may, in particular, be provided.

As regards the perfume concentrate used in the lipophilic phase, its concentration will vary in practice between approximately 8 and 20% by weight if it is desired to enter the product in the category of "toilet perfume" or "perfume water", and between approximately 15 and 30% by weight if it is desired to enter this same product in the category of "perfumes" or "perfume extracts".

Among the components of the different types of perfumes which may be used, there may be mentioned, in particular: complex mixtures of a plurality of organic compounds such as odoriferous essential oils, esters, ethers, aldehydes, certain alcohols and hydrocarbons (apart from saturated hydrocarbons having a number of carbon atoms below 10 or above 20), ketones, lactones and also other classes of components such as pyrrones and pyrroles. For a still more detailed list, reference may be made to the publication EP-A-0,368,146 (priority U.S.-88/267,872), the content of which, as regards the perfuming components which can be used, is included in the present description by reference.

As an additional constituent, the microemulsion may, furthermore, include in its fatty phase a lipid portion, which can thus consist of any liquid, oily compound in common use for pharmaceutical and/or cosmetic applications (such as mineral, animal, vegetable or silicone oil, oil based on organic fatty acid ethers, etc.), it being possible for the use of lipid compounds having a hydrophilic/lipophilic balance (HLB) in the region of 2 to prove advantageous.

Naturally, the distinction between the lipid and lipophilic portions will become more marked as the content of perfume concentrate increases and that of the "oil" decreases, it being possible for this oil to enable the HLB to be varied and for a silky appearance to be promoted when the product is deposited, for example, on the hair.

Turning now to the hydrophilic or aqueous phase, its composition may contain, apart from water or aqueous compound, preservatives, humectants and active principles, which active principles could also, in some cases, belong to the fatty phase.

As is well known, preservatives or antiseptics are intended for protecting a composition (in the present instance the microemulsion) against, in particular, microbial attack. They can include, in particular, parabens, such as methyl para-hydroxybenzoate (methyl paraben) and propyl para-hydroxybenzoate, imidazolidinylurea, etc. For any more detailed description, reference may be made to U.S. Pat. No. 4,917,891, the content of which (as regards the preservatives) is included by reference.

As regards humectants, intended for retaining moisture at the surface of the skin, polyols or polyhydric alcohols such as glycerol, sorbitol, propylene glycol, etc., may be mentioned in particular.

As regards the active principles, they will be defined as being formed, basically, from any raw material of vegetable, animal or synthetic origin participating in the composition of a cosmetic, usually other than excipients, and having biological properties favorable to the human epidermis, such as properties of hydration of the superficial layers of the epidermis or of cellular regeneration, or alternatively demulcent, emollient, cleansing, soothing, etc., properties. It hence relates both to vitamins and to essential fatty acids, vegetable (for example macadamia, sweet almond, borage, etc.) oils, animal oils (for example squalane), enzymes (SOD), glycosaminoglycans (such as hyaluronic acid) and more or less purified proteins (such as collagen, elastin, etc.).

In practice, active principles are thus often used to impart to the skin properties of hydration (glycosaminoglycans, essential fatty acids, etc.), of suppleness and elasticity (vegetable oil, protein, etc.) or of protection against a metabolic dysfunction or alternatively against the deleterious effects of ultraviolet radiation.

The mixing of these different compounds will be performed, generally speaking, in proportions which are determined beforehand by experience, without any special precaution or specific order, in particular at room temperature and with gentle stirring, it being possible for the microemulsion, depending upon requirements, to be of the oil-in-water or water-in-oil kind.

The examples which follow, given without implied limitation, enable some conditions of conclusive trials to be appraised.

EXAMPLE 1

Emollient Toilet Water

The following are mixed at room temperature in a beaker:
- 10 to 15 g of surfactant polyglycol ester of $C_8$–$C_{10}$ glycerides,
- 1 to 3 g of cosurfactant polyglyceryl dioleate,
- 0.5 to 2 g of cosurfactant DEA polyoxyethylene oleyl ether phosphate,
- 10 g of vegetable oil,
- 4 to 5 g of perfume concentrate,
- 0.2 g of preservative,
- qs 100 g of demineralised water.

After approximately 15 minutes' stirring at slow speed at room temperature (20° to 25° C.), a fluid and transparent microemulsion is obtained.

EXAMPLE 2

Perfume Water

The following are mixed at room temperature in a beaker:
- 20 to 26 g of surfactant polyglycol ester of glyceryl stearate,
- 2 to 6 g of cosurfactant polyglyceryl dioleate,
- 1 to 6 g of cosurfactant DEA polyoxyethylene oleyl ether phosphate,
- 15 g of perfume concentrate,
- 4 g of vegetable oil,
- 1 g of protein extract,
- 0.2 g of preservative,
- qs 100 g of demineralised water.

After approximately 15 minutes' stirring at slow speed at room temperature, a fluid and transparent microemulsion is obtained.

EXAMPLE 3

Alcohol-Free Perfume

The following are mixed at room temperature in a beaker:
- 30 to 50 g of surfactant polyglycol ester of glyceryl stearate,
- 10 to 15 g of cosurfactant polyglyceryl isostearate,
- 4 to 10 g of cosurfactant sodium polyoxyethylene oleyl ether phosphate,
- 30 to 50 g of perfume concentrate,
- 0.2 g of preservative,
- qs 100 g of demineralised water.

After approximately 30 minutes+ moderate stirring at room temperature, a transparent microemulsion is obtained.

EXAMPLE 4

Perfume Essence

The following are mixed at room temperature in a beaker:
- 40 g of perfume concentrate,
- 10 to 15 g of surfactant polyglycol ester of $C_8$–$C_{10}$ glycerides,
- 12 to 20 g of cosurfactant polyglyceryl isostearate,
- 8 to 15 g of cosurfactant DEA polyoxyethylene oleyl ether phosphate,
- 15 g of vegetable oil,
- 0.2 g of preservative,
- qs 100 g of demineralised water.

After approximately 15 minutes' stirring at slow speed at room temperature, a stable, fluid and transparent microemulsion is obtained.

All of these microemulsions can be presented in a variety of forms, such as traditional microemulsions, foam, aerosol, pressurised form, etc., with excellent stability at the normal temperatures at which they are used (that is to say in a range extending from $-30°$ C. to $+80°$ C. approximately), and are clear in nature, making them usable most especially in cosmetic applications to the face and body or in the hair.

We claim:

1. A cosmetic microemulsion comprising a mixture of:
   a perfume, on a weight basis of about 5% to 50% of the microemulsion;
   polyethylene glycol, on a weight basis of about 10% to 50% of the microemulsion;
   polyglycerol, on a weight basis of about 1% to 20% of the microemulsion;
   ether phosphate, on a weight basis of about 0.5% to 15% of the microemulsion;
   at least one lipophilic compound; and
   at least one hydrophilic compound, qs 100.

2. The microemulsion set forth in claim 1, wherein the hydrophilic compound is selected from the group consisting of water, preservatives, humectants, antiseptics, skin active principles; and
   wherein the lipophilic compound is selected from the group consisting of oils, silicones, and skin active principles.

3. The microemulsion set forth in claim 1 wherein the perfume is non-alcoholic-13 containing no saturated hydrocarbons with a number of carbon atoms below 10 or above 20, and bearing a hydroxyl function replacing a hydrogen atom.

4. The microemulsion set forth in claim 1 wherein the ether phosphate is an alkyl ether phosphate containing polyethoxylated fatty alcohols.

5. The microemulsion set forth in claim 1 wherein the perfume is non-lipid while processing an affinity for lipids.

6. The microemulsion set forth in claim 1 wherein the hydrophilic compound is non-alcoholic—containing no saturated hydrocarbons with a number of carbon atoms below 10 or above 20, and bearing a hydroxyl function replacing a hydrogen atom.

7. The microemulsion set forth in claim 1 wherein the lipophilic compound is non-alcoholic—containing no saturated hydrocarbons with a number of carbon atoms below 10 or above 20, and bearing a hydroxyl function replacing a hydrogen atom.

8. The microemulsion set forth in claim 1 wherein:
   the polyethylene glycol is selected from the group consisting of polyglycol ester of C8–C10 glyceride and polyglycol ester of glyceryl stearate; and
   the ether phosphate is selected from the group consisting of DEA polyoxyethylene oleyl ether phosphate and sodium polyoxyethylene oleyl ether phosphate.

9. A cosmetic microemulsion comprising:
   a hydrophilic phase;
   a lipophilic phase; and
   emulsifying agents for forming a water-in-oil microemulsion, and wherein—
   the lipophilic phase comprises a perfume, on a weight basis of about 5% to 50% of the microemulsion;
   the emulsifying agents comprise polyethylene glycol, on a weight basis of about 10% to 15% of the microemulsion;
   polyglycerol, on a weight basis of about 1% to 20% of the microemulsion;
   ether phosphate, on a weight basis of about 0.5% to 15% of the microemulsion;
   the hydrophilic phase consisting essentially of aqueous compounds, qs 100.

10. A cosmetic microemulsion comprising:
    a hydrophilic phase;
    a lipophilic phase; and
    emulsifying agents for forming an oil-in-water microemulsion, and wherein—
    the lipophilic phase comprises a perfume, on a weight basis of about 5% to 50% of the microemulsion;
    the emulsifying agents comprise polyethylene glycol, on a weight basis of about 10% to 15% of the microemulsion;
    polyglycerol, on a weight basis of about 1% to 20% of the microemulsion;
    ether phosphate, on a weight basis of about 0.5% to 15% of the microemulsion;
    the hydrophilic phase consisting essentially of aqueous compounds, qs 100.

11. The microemulsion set forth in claim 9 wherein the perfume is non-alcoholic—containing no saturated hydrocarbons with a number of carbon atoms below 10 or above 20, and bearing a hydroxyl function replacing a hydrogen atom.

12. The microemulsion set forth in claim 10 wherein the perfume is non-alcoholic—containing no saturated hydrocarbons with a number of carbon atoms below 10 or above 20, and bearing a hydroxyl function replacing a hydrogen atom.

* * * * *

UNITED STATES PATENT AND TRADEMARK OFFICE
CERTIFICATE OF CORRECTION

PATENT NO. : 5,252,555
DATED : October 12, 1993
INVENTOR(S) : Nathalie DARTNELL et al It is certified that error appears in the above-identified patent and that said Letters Patent is hereby corrected as shown below:

Column 7, claim 3, line 2, "non-alcoholic-13 containing" should read
--non-alcoholic-containing--.

Signed and Sealed this

Twenty-sixth Day of July, 1994

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,252,555

DATED : October 12, 1993

INVENTOR(S) : Nathalie Dartnell, et al

It is certified that error appears in the above-indentified patent and that said Letters Patent is hereby corrected as shown below:

Column 7, line 9, change "non-alcoholic-13 containing" to --non-alcoholic-containing--.

Column 8, line 6, change "15%" to --50%--.

Column 8, line 22, change "15%" to --50%--.

This certificate supersedes Certificate of Correction issued July 26, 1994.

Signed and Sealed this

Twentieth Day of December, 1994

Attest:

BRUCE LEHMAN

*Attesting Officer*     *Commissioner of Patents and Trademarks*